US00PP31535P3

(12) United States Plant Patent

Lewis et al.

(10) Patent No.: US PP31,535 P3
(45) Date of Patent: Mar. 10, 2020

(54) *CANNABIS* PLANT NAMED 'LEMON CRUSH OG'

(50) Latin Name: ***Cannabis* hybrid**
Varietal Denomination: LEMON CRUSH OG

(71) Applicant: Biotech Institute LLC, Westlake Village, CA (US)

(72) Inventors: Mark A. Lewis, Westlake Village, CA (US); Steven Haba, Westlake Village, CA (US)

(73) Assignee: Biotech Institute LLC, Westlake Village, CA (US)

( * ) Notice: Subject to any disclaimer, the term of this patent is extended or adjusted under 35 U.S.C. 154(b) by 0 days.

(21) Appl. No.: 15/932,562

(22) Filed: Mar. 16, 2018

(65) Prior Publication Data

US 2019/0183003 P1 Jun. 13, 2019

Related U.S. Application Data

(60) Provisional application No. 62/596,561, filed on Dec. 8, 2017.

(51) Int. Cl.
*A01H 5/02* (2018.01)
*A01H 6/28* (2018.01)
*A61K 36/185* (2006.01)

(52) U.S. Cl.
USPC ..... Plt./258
CPC ..... *A01H 6/28* (2018.05); *A61K 36/185* (2013.01)

(58) Field of Classification Search
USPC ..... Plt./258, 263.1
CPC ... A01H 5/12; A01H 5/00; A01H 6/28; A01H 5/02
See application file for complete search history.

(56) References Cited

U.S. PATENT DOCUMENTS

| | | | |
|---|---|---|---|
| 9,095,554 | B2 | 8/2015 | Lewis et al. |
| 9,370,164 | B2 | 6/2016 | Lewis et al. |
| PP27,475 | P2 | 12/2016 | Kubby |
| 9,642,317 | B2 | 5/2017 | Lewis et al. |
| 2014/0287068 | A1 | 9/2014 | Lewis et al. |
| 2014/0298511 | A1 | 10/2014 | Lewis et al. |
| 2015/0359188 | A1 | 12/2015 | Lewis et al. |
| 2015/0366154 | A1 | 12/2015 | Lewis et al. |
| 2016/0324091 | A1 | 11/2016 | Lewis et al. |
| 2017/0202170 | A1 | 7/2017 | Lewis et al. |
| 2018/0064055 | A1 | 3/2018 | Lewis et al. |
| 2018/0143212 | A1 | 5/2018 | Lewis et al. |

FOREIGN PATENT DOCUMENTS

| | | | |
|---|---|---|---|
| WO | WO 2014/145490 | A2 | 9/2014 |
| WO | WO 2015/065544 | A1 | 5/2015 |
| WO | WO 2016/105514 | A1 | 6/2016 |
| WO | WO 2016/123160 | A1 | 8/2016 |
| WO | WO 2018/094359 | A1 | 5/2018 |

OTHER PUBLICATIONS

Grasscity Forums 2010 Lemon Crush, retrieved on May 1, 2019, retrieved from the Internet at https://forum.grasscity.com/threads/lemon-crush-weed.475046/, 7 pp. (Year: 2010).*

* cited by examiner

*Primary Examiner* — June Hwu
(74) *Attorney, Agent, or Firm* — Cooley LLP

(57) ABSTRACT

The present invention provides a new and distinct cannabis cultivar designated as 'LEMON CRUSH OG'. The main terpenes found in 'LEMON CRUSH OG' are limoene, beta-caryophyllene, alpha-humulene, linalool, trans-ocimene, beta-pinene, fenchol, alpha-terpineol, alpha-pinene and myrcene. The estimated concentration of the total $THC_{max}$, $CBD_{max}$, and $CBG_{max}$ is about 18.77-23.19%, about 0%, and about 0.98-1.78%, respectively, at the time of assaying metabolites from flower samples of 'LEMON CRUSH OG'. Harvest interval, i.e. at 56-70 days under short day conditions.

14 Drawing Sheets

Latin name of genus and species: *Cannabis* hybrid.
Variety denomination: 'LEMON CRUSH OG'.

BACKGROUND OF THE INVENTION

The present invention relates to a new and distinct *cannabis* cultivar designated as 'LEMON CRUSH OG'.

This new cultivar is the result of controlled-crosses between proprietary cultivars made by the inventors. The new cultivar of 'LEMON CRUSH OG' was asexually reproduced via a stem 'cutting' and 'cloning' method by the inventors at Salinas, Calif. Asexual clones from the original source have been tested in greenhouses, nurseries, and/or fields. The properties of each cultivar were found to be transmissible by such asexual reproduction. The cultivar is stable and reproduces true to type in successive generations of asexual reproduction.

TAXONOMY AND NOMENCLATURE

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *cannabis* nomenclature is often used incorrectly or interchangeably. *Cannabis* literature can be found referring to all *cannabis* varieties as "*sativas*" or all cannabinoid producing plants as "*indicas*".

Indeed the promiscuous crosses of indoor *cannabis* breeding programs have made it difficult to distinguish varieties, with most *cannabis* being sold in the United States having features of both *sativa* and *indica* species.

Human cultivation history of *Cannabis* dates back 8000 years (Schultes, R E. 1970, Random thoughts and queries on the botany of *Cannabis*. Pages 11-38 in: CRB Joyce, and S H Curry eds., THE BOTANY AND CHEMISTRY OF *CANNABIS*. J. & A. Churchill. London, England). Hemp cloth recovered in Europe dates back 6000 years. (Small, E, Beckstead, H D, and Chan, A, 1975, The evolution of cannabinoid phenotypes in *Cannabis*, ECONOMIC BOTANY 29(3): 219-232. The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3), 304-310; Small, E and Cronquist, A, 1976, TAXON 25(4), 405-435; Small E and Cronquist, A, 1977, TAXON 26(1), 110; Hillig, K W and Mahlberg, P G, 2004, American Journal of Botany 91(6), 966-975, remains in question. This is in spite of the fact that its formal scientific name, '*Cannabis sativa* L.', assigned by Carolus Linneaus (Linnaeus, C, 1753, SPECIES PLANTARUM 2:1027, Salvius, Stockholm, Facsimile edition, 1957-1959, Ray Society, London, U.K.), is one of the oldest established names in botanical history and is still accepted to this day. Another species in the genus, '*Cannabis indica* Lam.' was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. saliva* was described as tall and laxly branched (Schultes R. E. et al, 1974, Harvard University Botanical Museum Leaflets, 23: 337-367). *C. indica* plants were also described as having short, broad leaflets whereas those of *C. saliva* were characterized as relatively long and narrow (Anderson L. C., 1980, Harvard University Botanical Museum Leaflets, 28: 61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* ('*C. sativa* ssp. *indica* Lam.'. Small and Cronquist 1976 Supra).

In the 20th century, two new names were added to the liturgy of proposed '*Cannabis* species: *C. ruderalis*' Janischevsky and a hybrid, x '*C. intersita*' Sojak. (Small, E, Jui, P Y, and Lefkovitch, L P, 1976, SYSTEMATIC BOTANY 1(1): 67-84; Small and Cronquist 1976, Supra). Further, numerous names have been proposed for horticultural variants of '*Cannabis*' but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5: 1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (Humulus), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. saliva* s., *C.* s. *indica*), each with two varieties (*C. s.* s. var. *saliva*, *C. s.* s. var. *spontanea; C. s.* i. var. *indica, C. s.* i. var. *Kafiristanica*) largely on the basis of chemotaxonomy and interfertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

This invention relates to a new and distinctive *cannabis* cultivar designated as 'LEMON CRUSH OG'.

The objective of the breeding program which produced novel plants disclosed herein was primarily to develop a *cannabis* cultivar with its unique blend of various cannabinoids and/or terpenes for (a) medicinal effects such as improving appetite and reducing nausea, vomiting and/or chronic pain, as well as neurological and cardiovascular effects, (b) psychoactive effects such as increased motivation and energetic behavior rather than indifference, passiveness and lethargy, and (c) recreational effects with enhanced enjoyment such as food and aroma.

As used herein, the term "cultivar" is used interchangeably with "variety", "strain", and/or "clone".

*Cannabis* plants produce a unique family of terpenophenolic compounds. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. The *cannabis* plant has at least 545 distinct compounds that span 20 chemical classes including cannabinoids, terpenes, terpenoids, amino acids, nitrogenous compounds, simple alcohols, aldehydes, ketones, esters, lactones, acids, fatty acids, steroids, non-cannabinoid phenols, pigments, flavonoids, vitamins, proteins, enzymes, glycoproteins, and hydrocarbons. Terpenes and/or cannabinoids, in particular, have shown great potential in terms of medicinal value.

Terpenes and/or cannabinoids have been shown to be largely responsible for beneficial effects of a *cannabis* plant. In fact, each *cannabis* plant has the varying concentrations of medically viable compounds depending on different strains (genotypes) and their resulting chemotypes. Even a small variation in terpene and/or cannabinoid concentration can cause noticeable differences in the entourage and/or synergistic effects of a *cannabis* plant, which distinguishes one variety from another. Research shows that it relies heavily on the physiological effects produced by terpenes and/or cannabinoids.

Over 100 different kinds of terpenes have been identified in *cannabis* plants although not being as well-studied as cannabinoids they are instrumental in giving rise to the physiological and psychoactive effects in *cannabis*.

Terpenes are a large and diverse class of organic compounds, produced by a variety of plants. They are often strong smelling and thus may have had a protective function. Terpenes are an important component, not only influencing taste and smell of each *cannabis* strain but also influencing its effects on the mind and body of a subject such as humans and animals. Terpenes are a classification of organic molecules that are found in a wide variety of plants and animals. These molecules are known for their characteristic scents and flavors. The varying terpene concentrations found in *cannabis* plants directly influence the resulting taste and smell, as well as the observed effects. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids. The main terpenes found in *cannabis* plants include, but are not limited to, myrcene, limonene, caryophyllene, pinene, terpinene, terpinolene, camphene, terpineol, phellandrene, carene, humulene, pulegone, sabinene, geraniol, linalool, fenchol, borneol, eucalyptol, and nerolidol.

Cannabinoids are the most studied group of the main physiologically active secondary metabolites in *cannabis*. The classical cannabinoids are concentrated in a viscous resin produced in structures known as glandular trichomes. At least 113 different cannabinoids have been isolated from *cannabis* plants. The main classes of cannabinoids from *cannabis* include tetrahydrocannabinol (THC), cannabidiol (CBD), cannabigerol (CBG), and cannabinol (CBN). Cannabinoid can be at least one of a group comprising tetrahydrocannabinol (THC), cannabidiol (CBD), cannabigerol (CBG), cannabinol (CBN) cannabichromene (CBC), cannabinodiol (CBDL), cinnabicyclol (CBL), cannabivarin (CBV), tetrahydrocannabivarin (THCV), cannabidivarin (CBDV), cannabigerovarin (CBGV), cannabichromevarin (CBCV), cannabigerol monomethyl ether (CBGM), cannabielsoin (CBE), cannabicitran (CBT), cannabinol propyl variant (CBNV), cannabitriol (CBO), tetrahydrocannabinolic acid (THCA), tetrahydrocannabivarinic acid (THCVA), cannabidiolic acid (CBDA), cannabigerolic acid (CBGA) and cannabinerolic acid.

Most cannabinoids exist in two forms, as acids and in neutral (decarboxylated) forms. The acidic form of cannabinoids is designated by an "A" at the end of its acronym (i.e. THCA). The cannabinoids in their acidic forms (those ending in "-A") can be converted to their non-acidic forms through a process called decarboxylation when the sample is heated. The phytocannabinoids are synthesized in the plant as acidic forms. While some decarboxylation does occur in the plant, it increases significantly post-harvest and the kinetics increase at high temperatures (Flores-Sanchez and Verpoorte, 2008, Plant Cell Physiol. 49(12): 1767-1782). The biologically active forms for human consumption are the neutral forms. Decarboxylation is usually achieved by thorough drying of the plant material followed by heating it, often by combustion, vaporization, heating, or baking in an oven. Unless otherwise noted, references to cannabinoids in a plant include both the acidic and decarboxylated versions (e.g., CBD and CBDA).

The molecules lose mass through the process of decarboxylation. In order to find the total theoretical active cannabinoids, the acid forms should be multiplied by 87.7%. For example, THCA can be converted to active THC using the formula: THCA×0.877=THC. The maximum THC for the sample is: $THC_{max}$=(THCA×0.877)+THC. This method has been validated according to the principles of the International Conference on Harmonization. Similarly, CBDA can be converted to active CBD and the yield is determined using the yield formula: CBDA×0.877=CBD. Also the maximum amount of CBD yielded, i.e. max CBD for the sample is: $CBD_{max}$=(CBDA×0.877)+CBD. Additionally, CBGA can be converted to active CBG by multiplying 87.8% to CBGA. Thus, the maximum amount of CBG is: $CBG_{max}$=(CBGA×0.878)+CBG.

The biologically active chemicals found in plants, phytochemicals, may affect the normal structure or function of the human body and in some cases treat disease. The mechanisms for the medicinal and psychoactive properties of a *cannabis* plant, like any medicinal herb, produce the pharmacologic effects of its phytochemicals, and the key phytochemicals for a medical *cannabis* plant are cannabinoids and terpenes.

While Δ9-Tetrahydrocannabinol (THC) is also implicated in the treatment of disease, the psychotropic activity of THC makes it undesirable for some patients and/or indications.

Tetrahydrocannabinol, THC, is the primary psychoactive and medicinal cannabinoid and is the result of the decarboxylation of tetrahydrocannabinolic acid (THCA), its acidic precursor. THCA, (6ar,10ar)-1-hydroxy-6,6,9-trimethyl-3-pentyl-6a,7,8,10a-tetrahydro-6h-benzochromene-2-carboxylic acid, is found in the trichomes of the plant and converted into THC, which actually exists in only minute quantities in the living plant, after harvest and drying.

While Cannabigerol (CBG), is not considered psychoactive, it is known to block the psychoactive effects of THC and is considered medically active in a variety of conditions. Its precursor, cannabigerolic acid, CBG-A, (E)-3-(3,7-Dimethyl-2,6-octadienyl)-2,4-dihydroxy-6-pentylbenzoic acid, is being studied medically.

Delta-9-Tetrahydrocannabinol or (THC) is a psychoactive cannabinoid responsible for many of the effects such as mild to moderate pain relief, relaxation, insomnia and appetite stimulation. THC has been demonstrated to have antidepressant effects. The majority of strains range from 12-21% THC with very potent and carefully prepared strains reaching even higher.

Cannabidiol (CBD) is one of the principal cannabinoids found in a *cannabis* plant and is largely considered to the most medically significant. CBD occurs in many strains, at low levels, <1%. In some cases, CBD can be the dominant cannabinoid, as high as 15% by weight. CBD is non-psychoactive, meaning that unlike THC, CBD does not cause a noticeable "high". CBD has shown potential for the treatment of a wide variety of diseases and symptoms, including cancer, nausea, chronic pain, spasms, seizures/ epilepsy, anxiety, psoriasis, Crohn's disease, rheumatoid arthritis, diabetes, schizophrenia, post-traumatic stress disorder (PTSD), alcoholism, strokes, Multiple Sclerosis, and cardiovascular disease. CBD also has been reported to act as a muscle relaxant, antibiotic, anti-inflammatory, and bone stimulant, as well as to improve blood circulation, cause drowsiness, and protect the nervous system. It can provide relief for chronic pain due to muscle spasticity, convulsions and inflammation, as well as effective relief from anxiety-related disorders. It can offer relief for patients with Multiple Sclerosis (MS), Fibromyalgia and Epilepsy. CBD has also been shown to inhibit cancer cell growth when injected into breast and brain tumors in combination with THC.

A *cannabis* cultivar can be used to achieve the desire of patients to be treated with CBD without the adverse side-effects (e.g., psychoactivity) of THC.

Cannabichromene (CBC) is a rare, non-psychoactive cannabinoid, usually found at low levels (<1%) when present. It has been shown to have anti-depressant effects and to improve the pain-relieving effects of THC. Studies have demonstrated that CBC has sedative effects such as promoting relaxation.

Cannabigerol (CBG) is a non-psychoactive cannabinoid. CBG-acid is the precursor to both THC-acid and CBD-acid in the plant usually found at low levels (<1%) when present. It has been demonstrated to have both pain relieving and inflammation reducing effects. CBG reduces intraocular pressure, associated with glaucoma. CBG has been shown to have antibiotic properties and to inhibit platelet aggregation, which slows the rate of blood clotting.

Cannabidiol (CBD) and cannabichromene (CBC) are both non-psychoactive and end products of CBG metabolism, like THC, that are used medically.

Cannabinol or (CBN) is an oxidative degradation product of THC. It may result from improper storage or curing and extensive processing, such as when making concentrates. It is usually formed when THC is exposed to UV light and oxygen over time. CBN has some psychoactive properties, less strength than THC. CBN is thought to enhance the dizziness and disorientation that users of *cannabis* may experience. It may cause feelings of grogginess, and has been shown to reduce heart rate.

High potency *cannabis* plants contain large quantities of specific terpenes as well as various assortments of other terpenes. For instance, a *cannabis* plant may have a profile with either a high level of, a moderate amount of or a small amount of various terpenes depending on its cultivar and environmental conditions.

Various cultivars of '*Cannabis*' species have been cultivated in an effort to create a cultivar best suited to meet the interest of inventors according to their own need. The particular plant disclosed herein was discovered in the area where the inventors were intentionally cross-pollinating and cultivating plants described below using standard Mendelian breeding procedures well known to those of ordinary skill in the art. This resulted in the progenies of the inventors' crosses.

The progenies resulting from any selection stage of either the crossing, selfing or backcrossing versions of the breeding regimes of the present invention were asexually reproduced to fix and maintain the desirable THC content, CBs content, terpenes content, the aroma and flavor(s) typical of the desired class, and the other desirable phenotypic and/or genotypic characteristics. The resultant selected *cannabis* cultivar is designated as 'LEMON CRUSH OG' disclosed herein.

The inventors reproduced progenies asexually by stem cutting and cloning. This is the origin of this remarkable new cultivar. The plant has been and continues to be asexually reproduced by stem cutting and cloning at the inventors' greenhouses, nurseries and/or fields in Salinas, Calif., Oakland, Calif., and/or Washington, D.C.

The following are the most outstanding and distinguishing chemical characteristics of this new cultivar when grown under normal conditions in Salinas, Calif. Chemical analyses of the new *cannabis* variety and the check variety (or the parental varieties) disclosed herein were performed using standard chemical separation techniques well known to those skilled in the art. Samples for assaying were obtained from flower tissues of the *cannabis* plant disclosed herein. Cannabinoid composition of this cultivar can be determined by assaying the concentration of at least one cannabinoid in a subset (e.g., sample) of the harvested product.

Table 1 includes detailed information of the *cannabis* plant named 'LEMON CRUSH OG' including the concentration ranges of terpenes and cannabinoids as tested on flowers sampled on at least four different dates. The *cannabis* plant has been tested in a laboratory setting and/or facility to determine cannabinoids and terpenes concentrations in the *cannabis* plant named 'LEMON CRUSH OG' according to the procedures provided in Giese et al. (Journal of AOAC International (2015) 98(6):1503-1522).

1) The main terpenes found in 'LEMON CRUSH OG' are limonene, beta-caryophyllene, alpha-humulene, linalool, trans-ocimene, beta-pinene, fenchol, alpha-terpineol, alpha-pinene and myrcene;
2) The estimated concentration of the total $THC_{max}$, $CBD_{max}$, and $CBG_{max}$ is about 18.77-23.19%, about 0%, and about 0.98-1.78%, respectively, at the time of assaying metabolites from flower samples of 'LEMON CRUSH OG'; and
3) Harvest interval, i.e. at 56-70 days under short day conditions.

Terpene and cannabinoid profiles of 'LEMON CRUSH OG' demonstrate that 'LEMON CRUSH OG' has a phenotypically unique profile, particularly insofar as to the level of terpenes and cannabinoids. This data is presented in tabular form in Table 1.

TABLE 1

| Ranges of Active Cannabinoids and Terpenes | | | |
|---|---|---|---|
| Ranges of Active Cannabinoids (% by weight) | | | |
| Max THC | 18.77-23.19% | Max CBD | 0.00% |
| Terpenes (% by weight) | | | |
| thujene | 0.00% | trans-ocimene | 0.15-0.33% |
| alpha-pinene | 0.09-0.17% | gamma-terpinene | 0.00% |
| camphene | 0.02-0.03% | linalool oxide | 0.00-0.01% |
| sabinene | 0.00% | terpinolene | 0.01-0.02% |
| beta-pinene | 0.14-0.20% | linalool | 0.20-0.44% |
| myrcene | 0.07-0.13% | fenchol | 0.09-0.16% |
| alpha-phellandrene | 0.00% | MT_1124 | 0.06-0.11% |
| carene | 0.00% | isoborneol | 0.00-0.02% |
| alpha-terpinene | 0.00% | (−) borneol | 0.02-0.04% |
| limonene | 0.81-1.26% | hexyl butyrate | 0.00% |
| beta-phellandrene | 0.00% | alpha-terpineol | 0.08-0.15% |
| cineole | 0.00-0.01% | hexyl hexanoate | N/A |
| cis-ocimene | 0.00-0.01% | citronellol | 0.00-0.01% |

TABLE 1-continued

| Ranges of Active Cannabinoids and Terpenes | | |
|---|---|---|
| Ranges of Active Cannabinoids (% by weight) | | |
| Max THC | Max CBG | 0.98-1.78% |
| Terpenes (% by weight) | | |
| thujene | hexyl hexanoate | 0.04-0.08% |
| alpha-pinene | octyl butyrate | 0.00% |
| camphene | beta-caryophyllene | 0.52-0.89% |
| sabinene | alpha-humulene | 0.31-0.50% |
| beta-pinene | cis-nerolidol | 0.00-0.02% |
| myrcene | trans-nerolidol | 0.00-0.04% |
| alpha-phellandrene | caryophyllene oxide | 0.01-0.02% |
| carene | alpha-bisabolol | 0.00-0.01% |
| alpha-terpinene | nerol | 0.00% |
| limonene | geraniol | 0.00% |
| beta-phellandrene | geranyl-acetate | 0.00-0.02% |
| cineole | methyl-eugenol | 0.00-0.02% |
| cis-ocimene | Total Terpenes | 3.23-4.07% |

The *cannabis* plant named 'LEMON CRUSH OG' has a complement of terpenes, including but not limited to, relatively high levels of limonene, beta-caryophyllene, alpha-humulene, linalool, trans-ocimene, beta-pinene, fenchol, alpha-terpineol, alpha-pinene and myrcene compared to other terpene compounds. This unique combination of differently concentrated terpenes further distinguishes 'LEMON CRUSH OG' from other varieties in its odor, its medical qualities, and its effects on mood and mentation.

Asexual Reproduction

Asexual reproduction, also known as "cloning", is a process well known to those of ordinary skill in the art of *cannabis* production and breeding and includes the following steps.

The *cannabis* cultivar disclosed herein is asexually propagated via taking cuttings of shoots and putting them in rock wool cubes. These cubes are presoaked with pH adjusted water and kept warm (~80° F.). Full trays are covered, left under 18 hours of light and allowed to root (7-14 days). Upon root onset, the plantlets are transplanted into rigid 1 gallon containers filled with a proprietary soil mix A and remain in 18 hours of daylight for another 14-21 days. Once root-bound, plants are transplanted into rigid 3 gallon containers filled with proprietary soil mix B. Immediately, the light cycle is altered to 12/12 and flower initiating begins. The plants remain in 12/12 lighting until harvesting. They undergo a propriety nutrient regimen and grow as undisturbed as possible for 60-70 days depending on chemotype analysis.

All sun leaves are removed and the plant is dismantled to result in approximately 12" branches covered in inflorescences and trichomes. The goal in harvesting is to actually harvest trichome heads but not 'buds'. Thus, great care is taken not to disturb the trichome heads and as much of the plant remains intact as possible to promote even and slow drying. Slow drying is followed by a one to two months curing process.

Observation of the all female progenies of the original plant has demonstrated that this new and distinct cultivar has fulfilled the objectives and that its distinctive characteristics are firmly fixed and hold true from generation to generation vegetatively propagated from the original plant.

Under careful observation, the unique characteristics of the new cultivar have been uniform, stable and reproduced true to type in successive generations of asexual reproduction.

DESCRIPTION OF THE DRAWINGS

The accompanying color photographs depict characteristics of the new 'LEMON CRUSH OG' plants as nearly true as possible to make color reproductions. The overall appearance of the 'LEMON CRUSH OG' plants in the photographs is shown in the colors that may differ slightly from the color values described in the detailed botanical description.

DETAILED BOTANICAL DESCRIPTION

Figure 1:
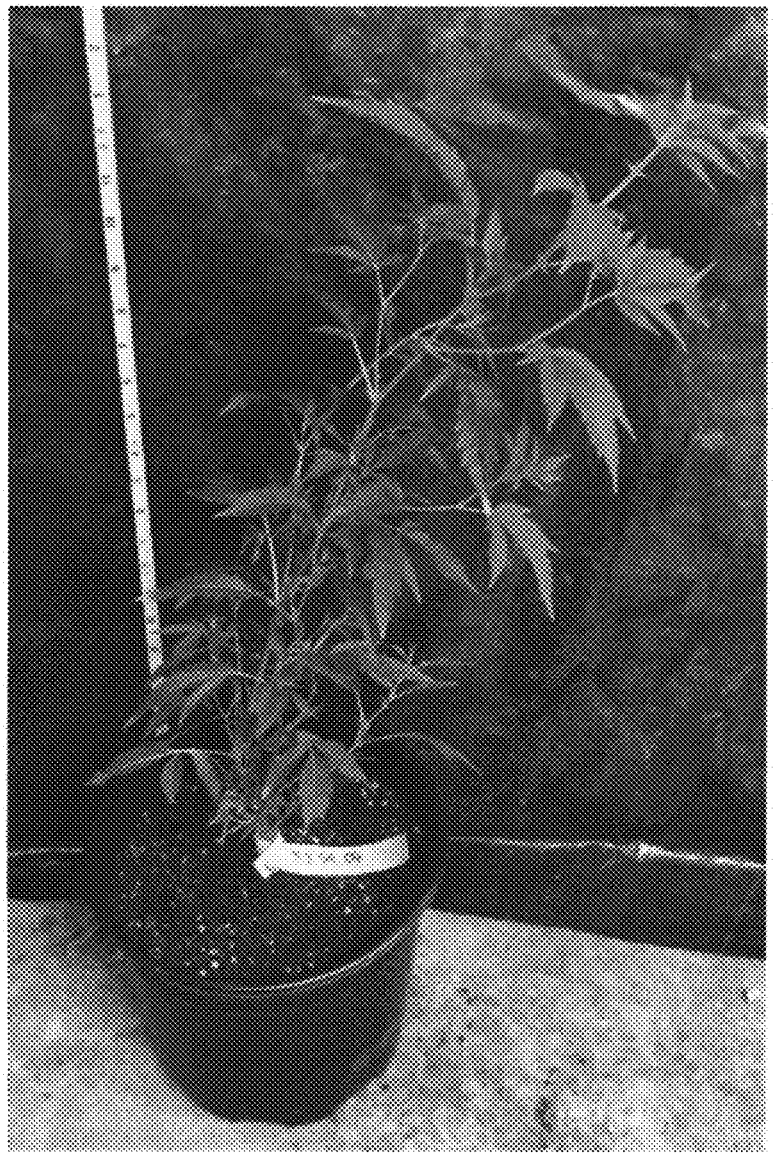
FIG. 1 shows an overall view of the 'LEMON CRUSH OG ' plant from the side.
Figure 2A:
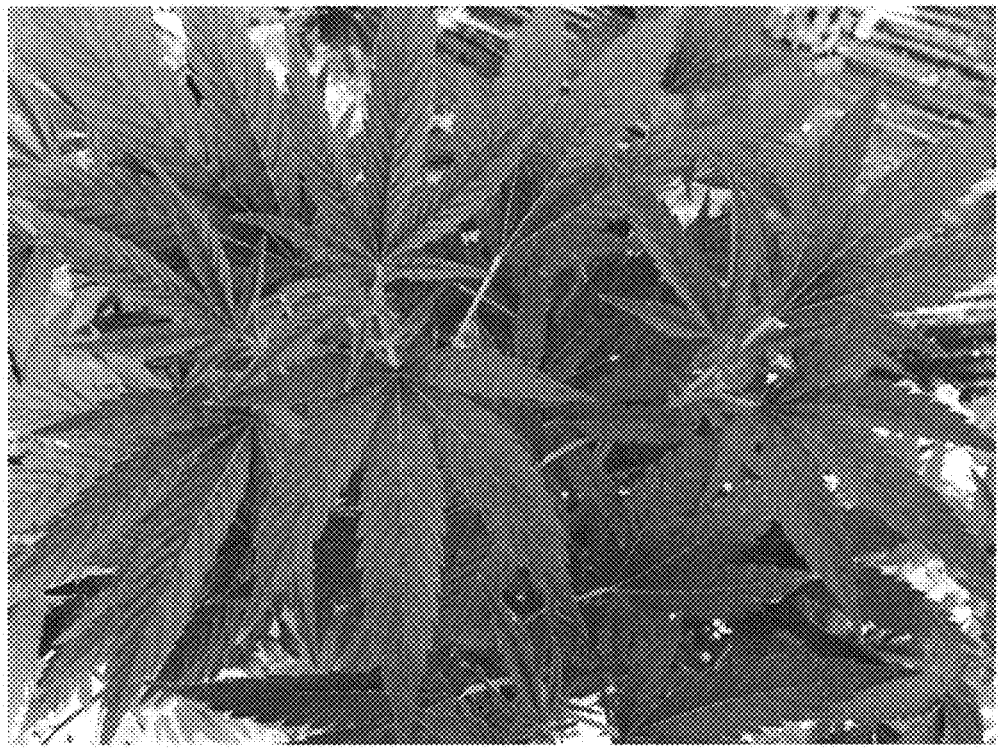
FIG. 2A shows an overall view of the female parental cultivar BLK03 (pollen acceptor; B3) from above.
Figure 2B:
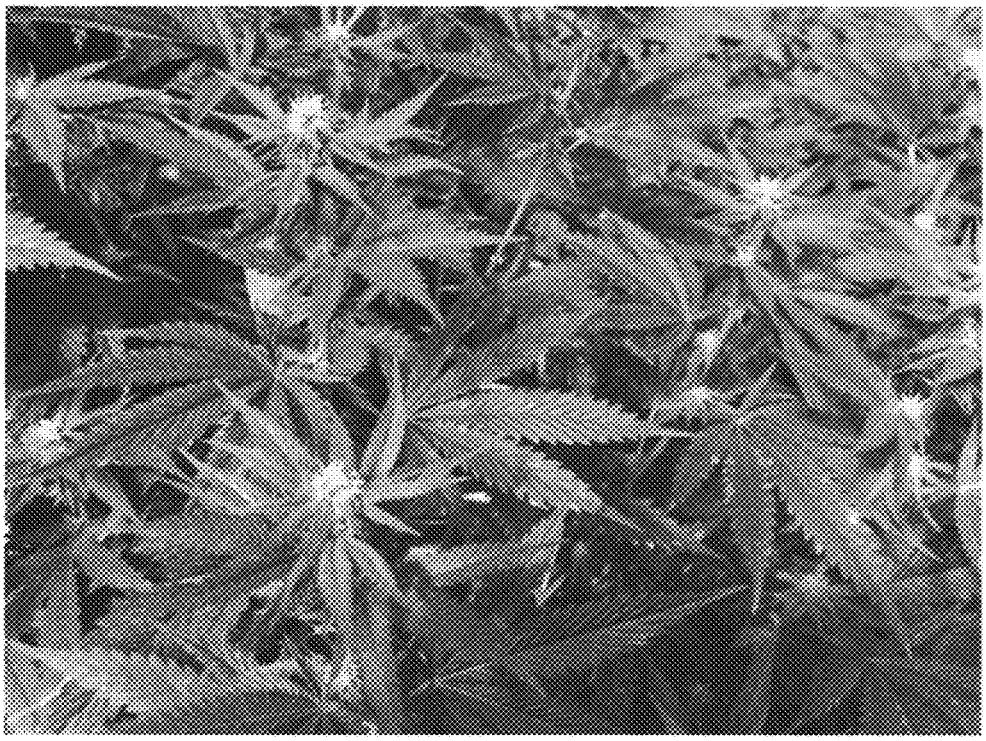
FIG. 2B shows an overall view of the male parental cultivar SLV09 (pollen donor; S9) from above.
Figure 2C:
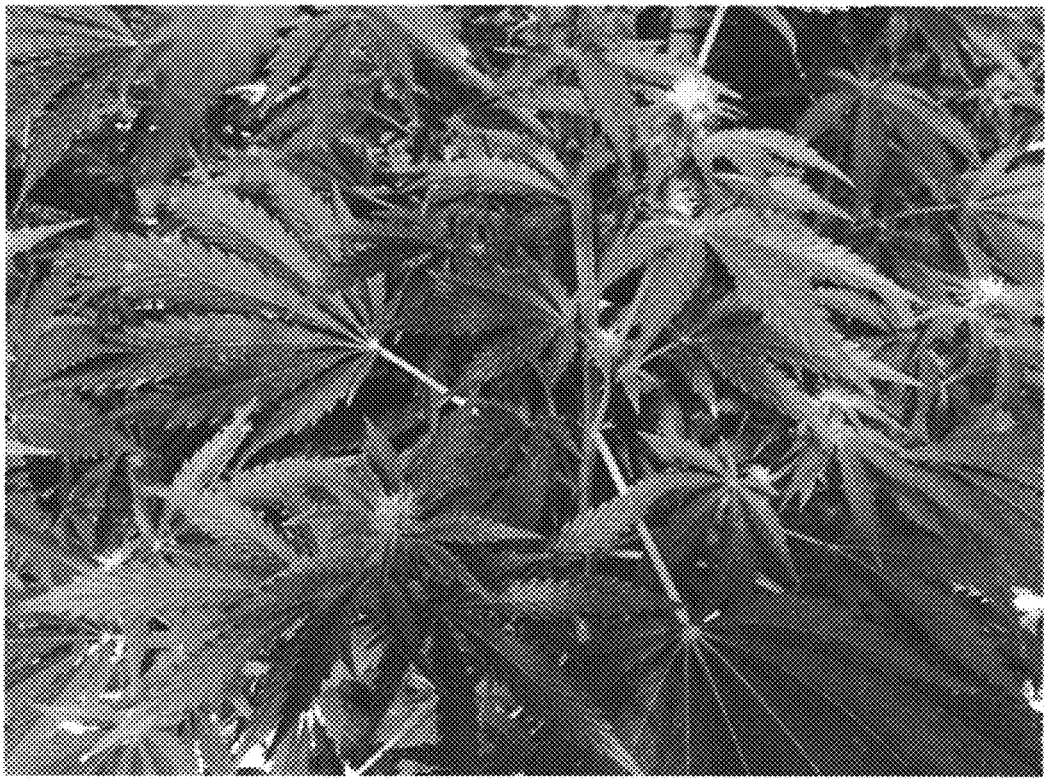
FIG. 2C shows an overall view of the 'LEMON CRUSH OG' plant from above.
Figure 3A:
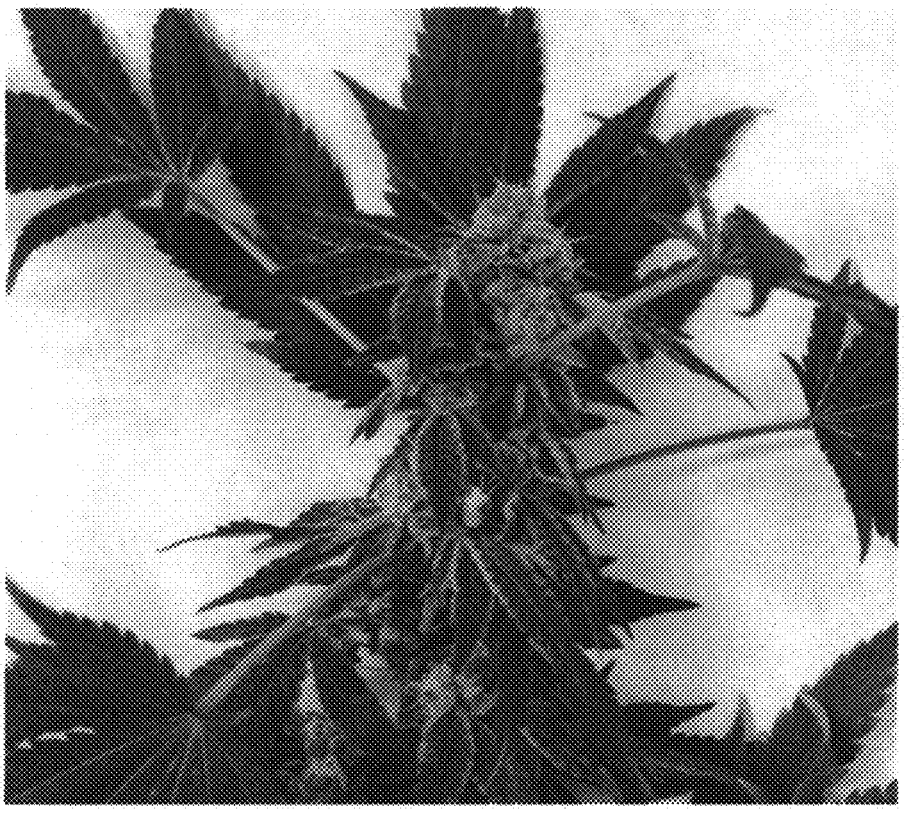
FIG. 3A shows top parts (including inflorescence) of the female parental cultivar BLK03 (pollen acceptor; B3) from the side.
Figure 3B:
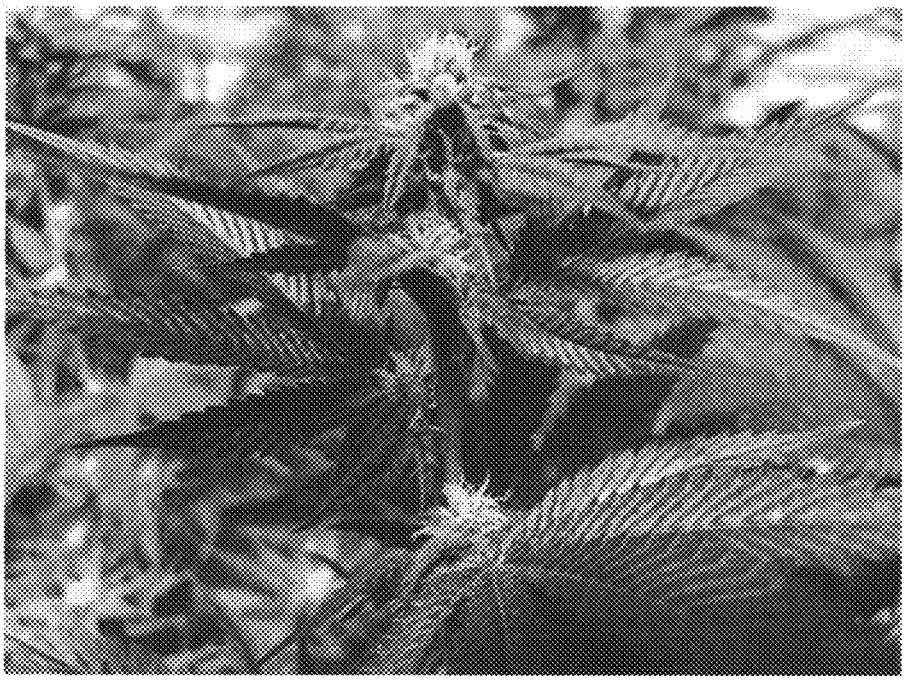
FIG. 3B shows top parts (including inflorescence) of the male parental cultivar SLV09 (pollen donor; S9) from the side.
Figure 3C:
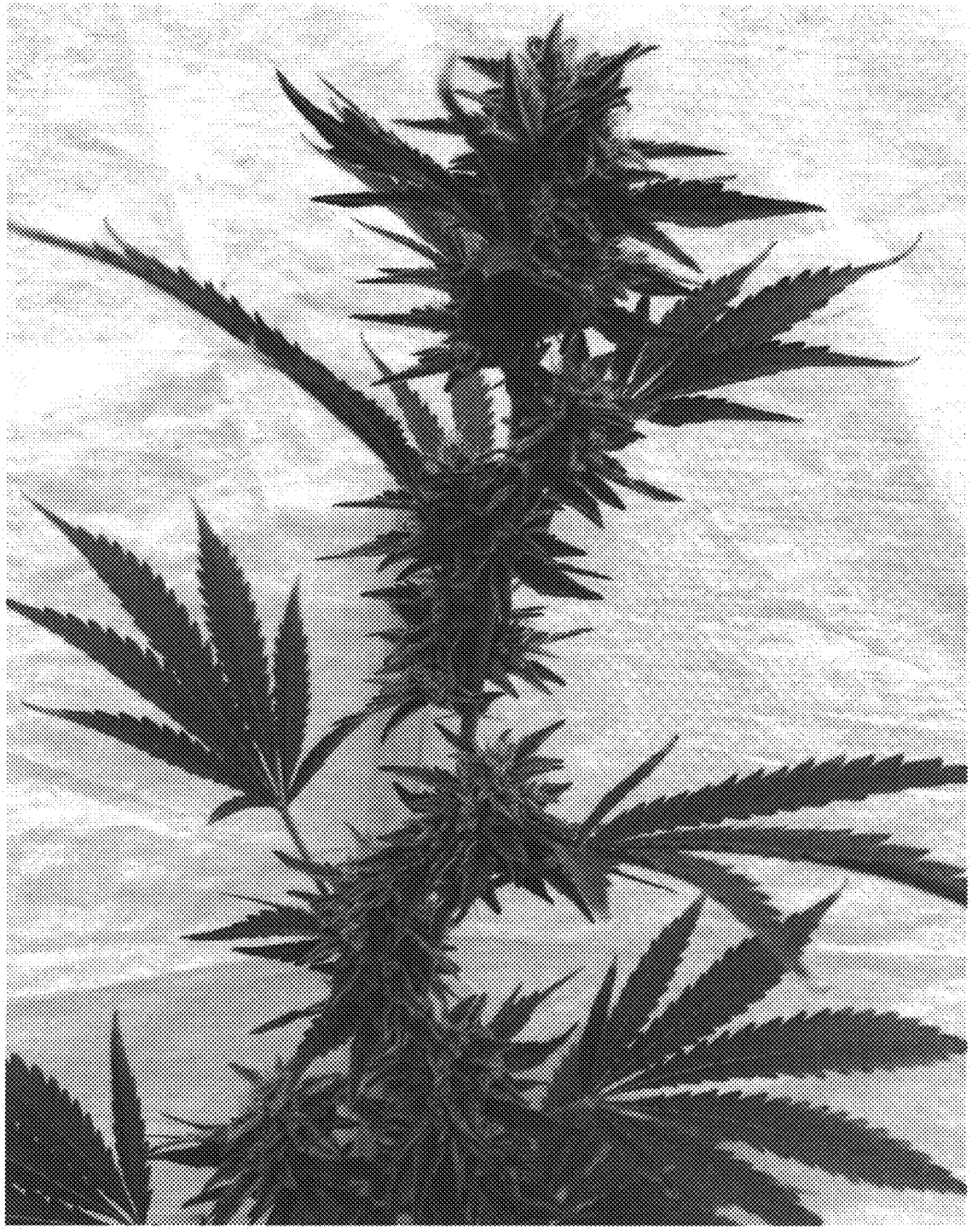
FIG. 3C shows top parts (including inflorescence) of the 'LEMON CRUSH OG' plant from the side.
Figure 4A:
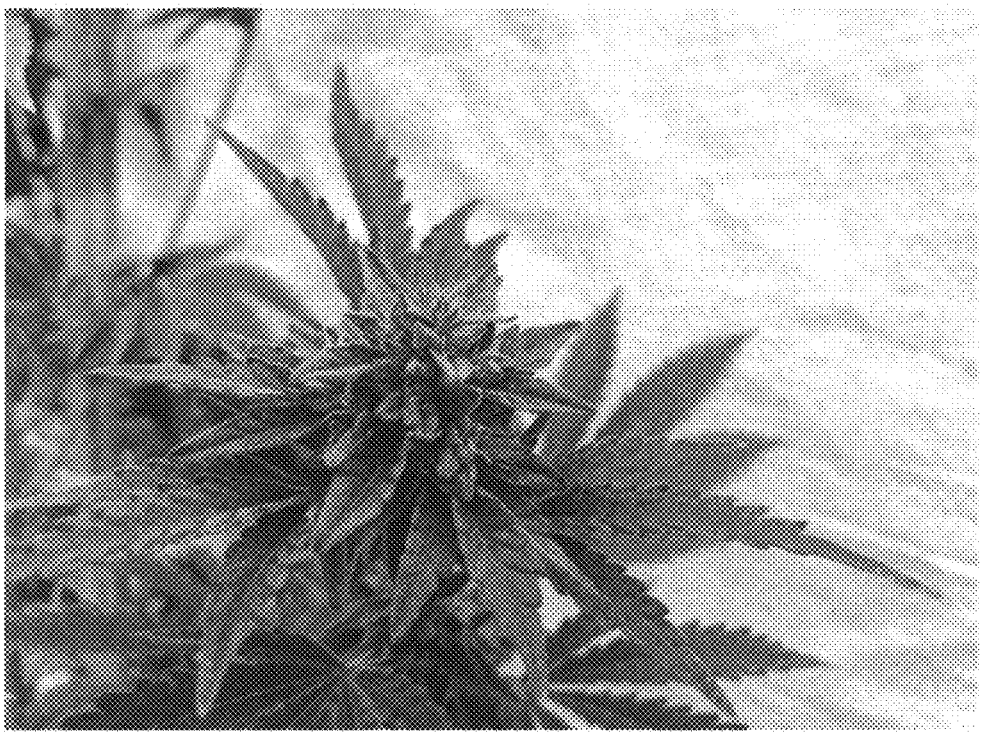
FIGS. 4A and 4B show a close view of flowers of the 'LEMON CRUSH OG' plant at premature and/or early floral stage.
Figure 4B:
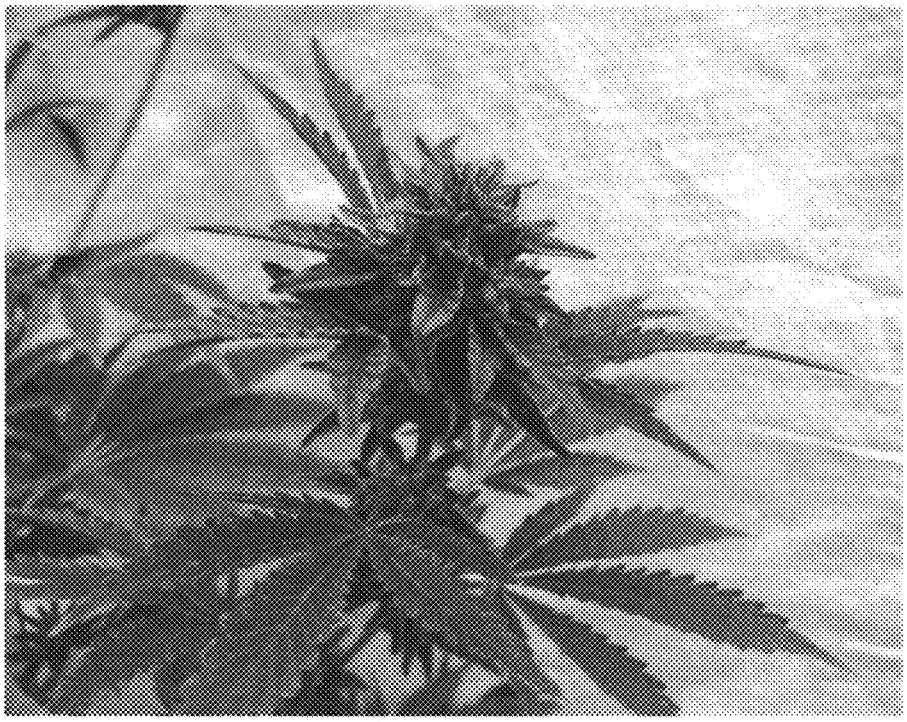
Figure 5A:
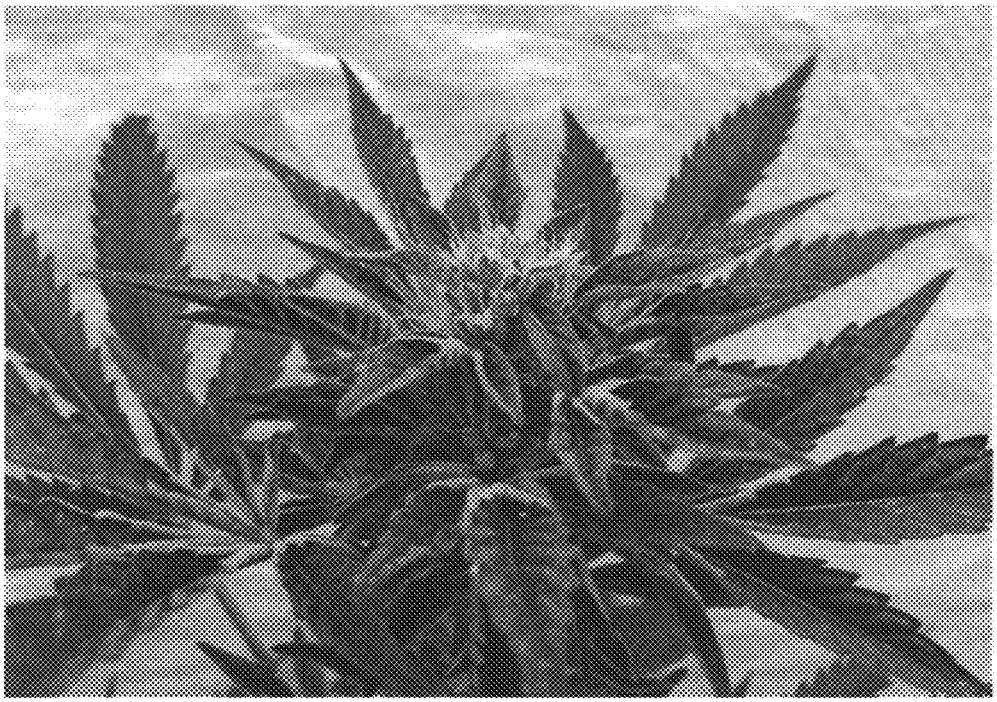
FIGS. 5A and 5B show a close view of flowers of the 'LEMON CRUSH OG' plant at the early and/or peak floral stage.
Figure 5B:
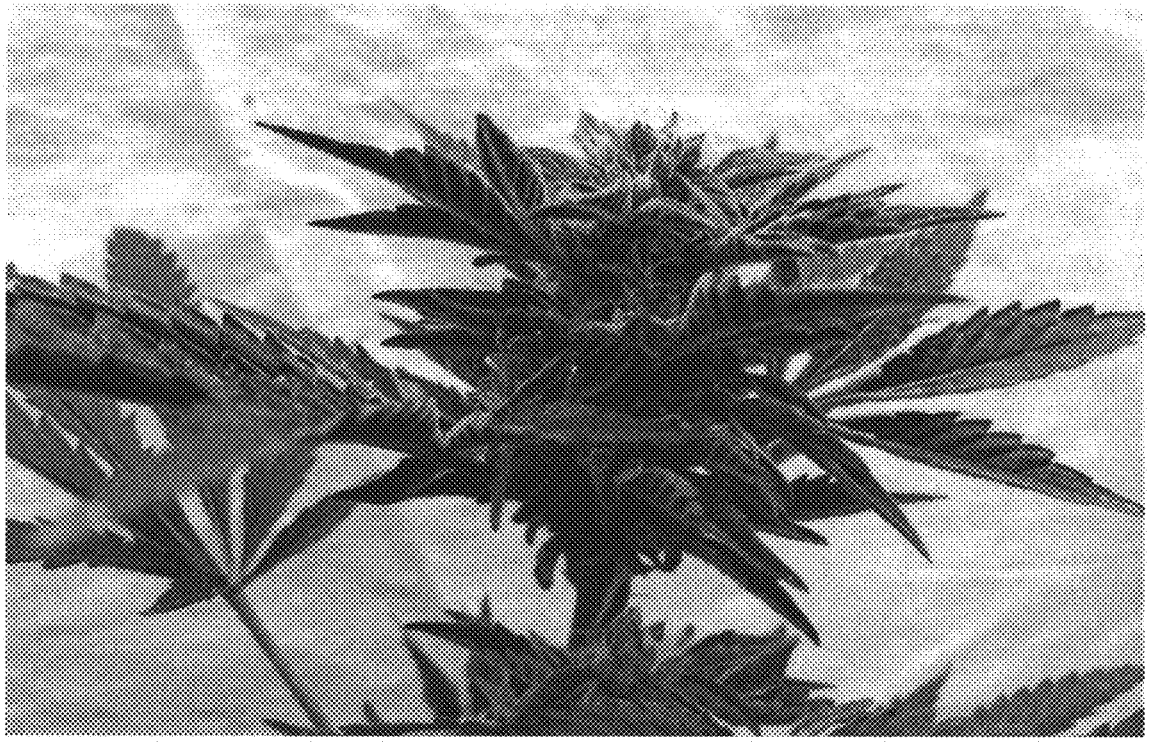
Figure 6A:
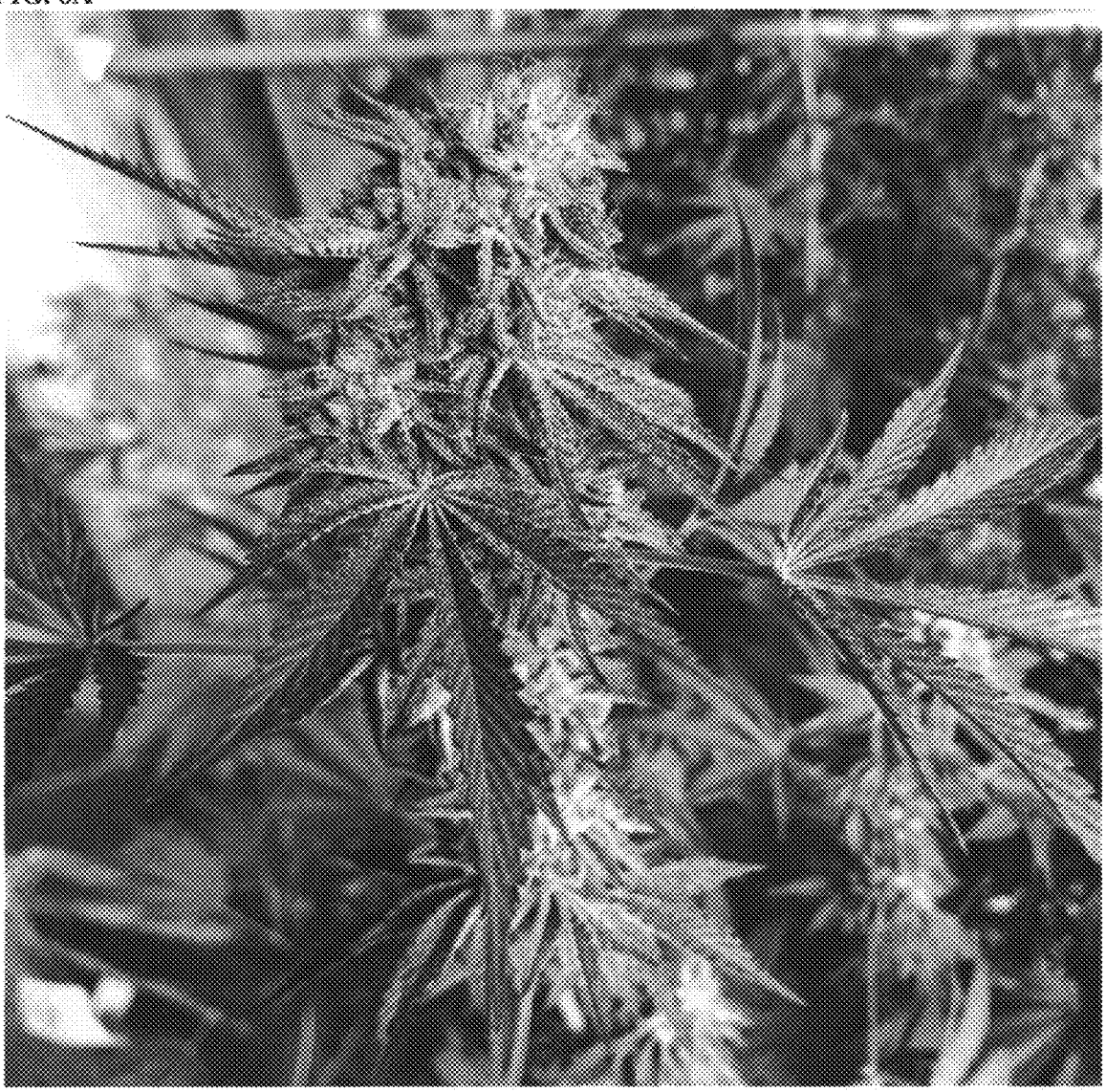
FIGS. 6A and 6B show a close view of flowers of the 'LEMON CRUSH OG' plant at the late floral and/or senescence stage.
Figure 6B:
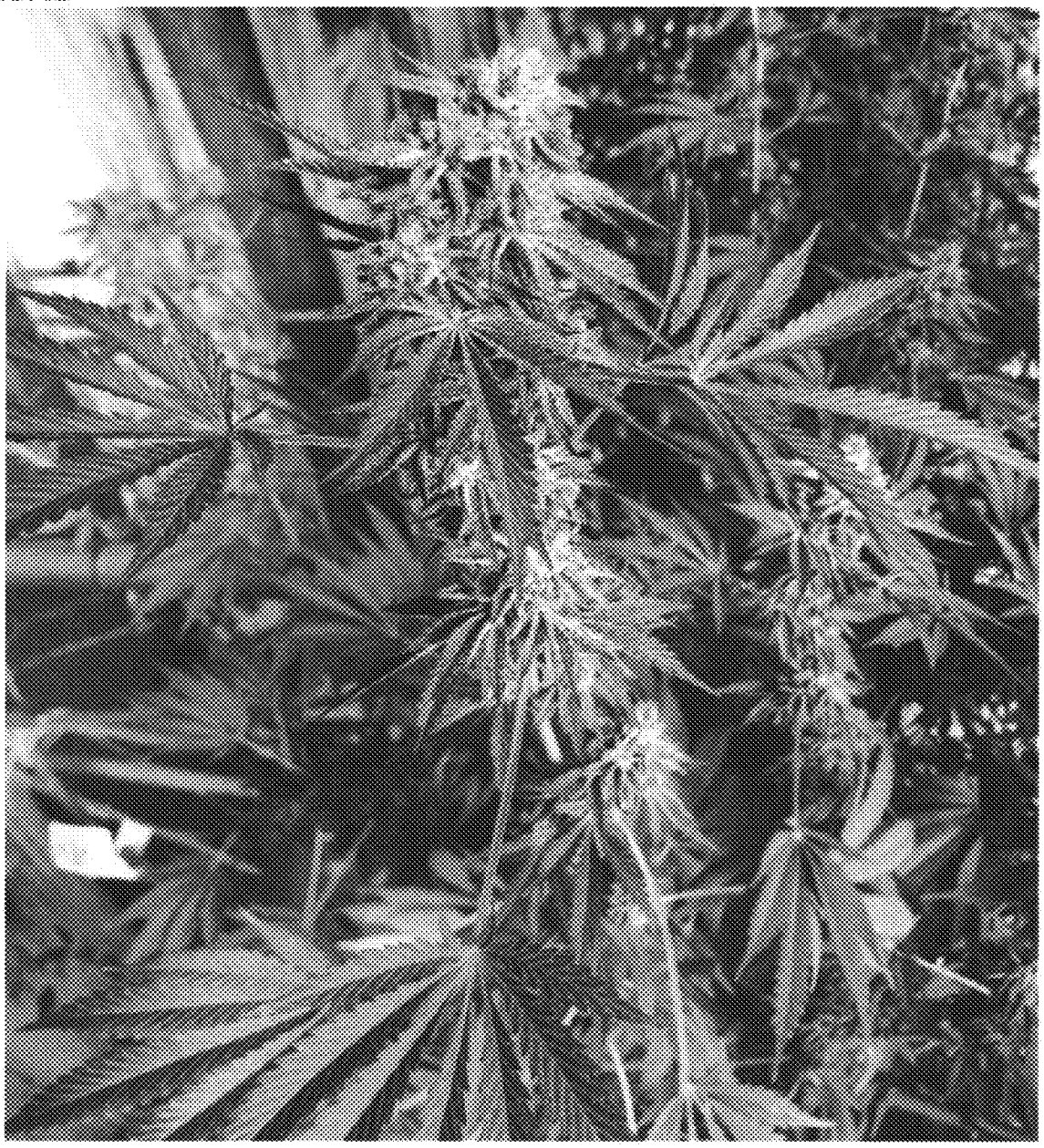
Figure 7:
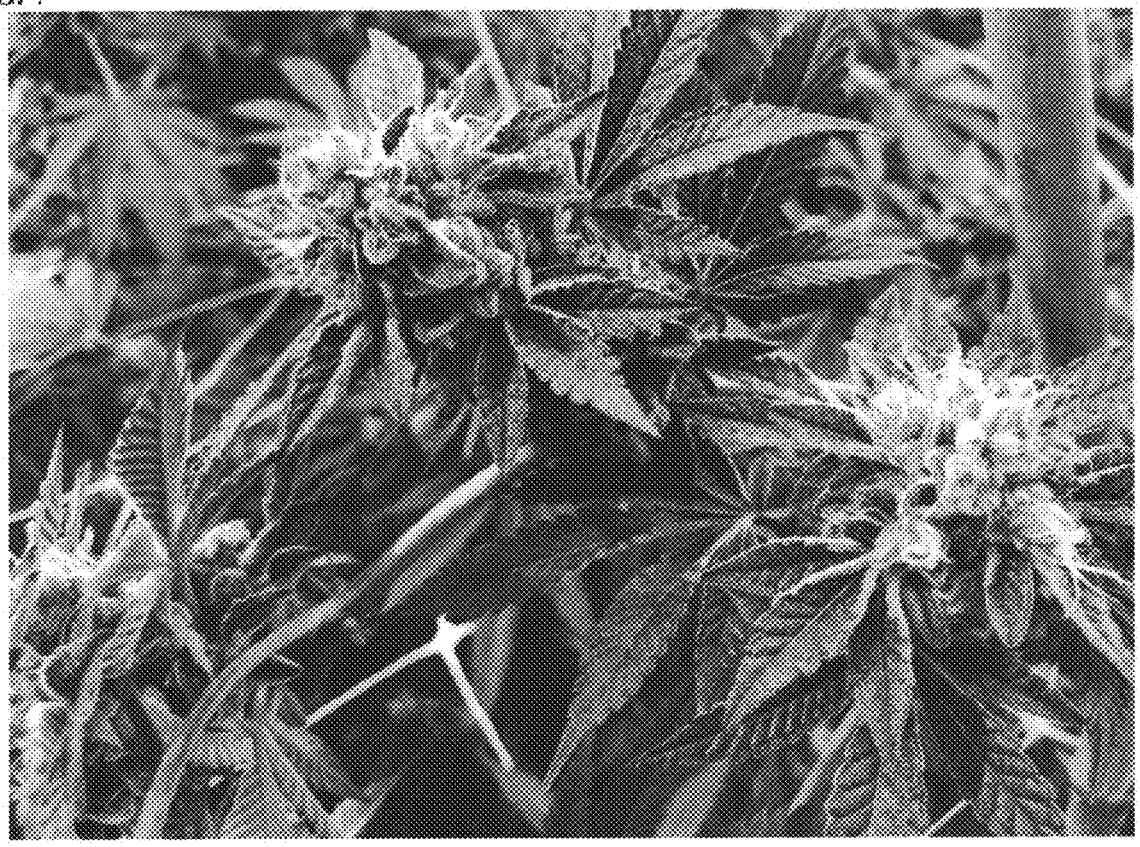
FIG. 7 shows another close view of flowers of the 'LEMON CRUSH OG' plant at the late floral and/or senescence stage.

'LEMON CRUSH OG' has not been observed under all possible environmental conditions, and the phenotype may vary significantly with variations in environment. The following observations, measurements, and comparisons describe this plant as grown at Salinas, Calif., when grown in the greenhouse, nursery or field, unless otherwise noted.

Plants for the botanical measurements in the present application are annual plants. In the following description, the color determination is in accordance with The Royal Horticultural Society Colour Chart, 2007 Edition, except where general color terms of ordinary dictionary significance are used.

The *cannabis* plant disclosed herein was derived from female and male parents that are said to have been internally designated as below.

A GNBR internal Code of the *cannabis* plant named 'LEMON CRUSH OG' is B3.S9.09. The variety name of 'LEMON CRUSH OG' is BLK03.SLV09.09. 'LEMON CRUSH OG' is a fertile hybrid derived from a controlled-cross between two proprietary cultivars BLK03 (pollen accepter; female parent; also known as B3) and SLV09 (pollen donor; male parent; also known as S9). A GNBR Breeding Code is (B03)x(S09).09. The initial cross between two parental cultivars was made in May 2015. The phenotypic criteria to select a new and distinct *cannabis* cultivar disclosed herein is as follows: structure score, nose/organoleptic, mold susceptibility/resistance, and insect susceptibility/resistance. Also, the first asexual propagation of 'LEMON CRUSH OG' occurred on Sep. 26, 2016 in Salinas, Calif.

The following traits in combination further distinguish the *cannabis* cultivar 'LEMON CRUSH OG' from check varieties, which are the female and male parents of the *cannabis* cultivar disclosed and claimed herein. Tables 2 to 6 present phenotypic traits and/or characteristics of 'LEMON CRUSH OG' compared to those of the parental check varieties, 'BLK03' (B3) and 'SLV09' (S9), as follows. 'BLK03' and 'B3' indicate the same female parental variety, while 'SLV09' and 'S9' indicate the same male parental variety. All plants were raised together and evaluated when 93-100 days old (i.e., the day range for propagation, vegetative, and flowering times).

TABLE 2

General Characteristics

| Characteristics | New Variety | Parental variety (B3) (Female plant) | Parental variety (S9) (Male plant) |
|---|---|---|---|
| Plant life forms | An herbaceous plant (herb) | An herbaceous plant (herb) | An herbaceous plant (herb) |
| Plant growth habit | An upright, tap-rooted annual plant | An upright, tap-rooted annual plant | An upright, tap-rooted annual plant |
| Plant origin | BLK03 (B3) × SLV09 (S9) | GLD13 × BSIA | (NL#5 × SB Purps) × (GlD13) |
| Plant propagation | Asexually propagated by stem cuttings and cloning | Asexually propagated by stem cuttings and cloning | Asexually propagated by stem cuttings and cloning |
| Propagation ease | Easy | Moderate | Moderate |
| Height | 1.5-4 m | 0.5-2.5 m | 2.0-3.5 m |
| Width | 89 cm | 119.5 cm | 56 cm |
| Plant vigor | High | Medium | Medium |
| Time to Harvest | 11 weeks | 8 weeks | 11 weeks |
| Resistance to pests or diseases | Resistant to pest as follows; (1) Two-spotted spider mite such as *Tetranychus urticae* (Koch); (2) Aphids species such as Cannabis Aphid (*Phorodon cannabis*), Green Peach Aphid (*Myzus persicae* (Sulzer)), Foxglove Aphid (*Aulacorthum solani*), Peach Aphid (*Macrosiphum euphorbiae*), and Black Bean Aphid (*Aphis fabae*); (3) Whitefly (*Trialeurodes vaporariorum*); (4) Lepidoptera species such as Armyworm (*Spodoptera frugiperda*); Cabbage Whites (*Pieris rapae*); Painted Lady (*Vanessa cardui*); and *Lepidoptera* sp. Resistant to Diseases: Botrytis/Flower Rot (*Botrytis cinerea*); Powdery Mildew (*Podosphaera xanthii*) | Resistant Non-Resistant to two spotted spider mite or aphids, whitefly, but resistant to Lepidoptera species | Resistant Non-Resistant to Aphid species, Lepidoptera, whitefly, but resistant to two spotted spider mite |
| Genetically-modified organism | NO | NO | NO |

TABLE 3

Leaf/Foliage

| Characteristics | New Variety | Parental variety (B3) (Female plant) | Parental variety (S9) (Male plant) |
|---|---|---|---|
| Leaf arrangement | Alternate | Alternate | Alternate |
| Leaf shape | Palmately compound | Palmately compound | Palmately compound |
| Leaf structure | Linear-lanceolate leaflet blades with glandular hairs | Linear-lanceolate leaflet blades with glandular hairs | Linear-lanceolate leaflet blades with glandular hairs |
| Leaf margins | Dentate, coarsely serrated, and the teeth point towards the tip | Dentate, coarsely serrated, and the teeth point towards the tip | Dentate, coarsely serrated, and the teeth point towards the tip |
| Leaf hairs | Present | Present | Present |
| Leaf length with petiole at maturity | 19.1 cm | 16.6 cm | 9.5 cm |
| Leaf width at maturity | 13.5 cm | 10.7 cm | 9.3 cm |
| Petiole length at maturity | 5.5 cm | 6.5 cm | 2.0 cm |
| Petiole color (RHS No.) | 149B | 140C | 149C |
| Intensity of petiole anthocyanin | Absent (vegetative stage); very strong (late flowering stage) | Present-Moderately (vegetative stage); very strong (late flowering stage) | Absent throughout entire life cycle |
| Stipule length at maturity | 0.5 cm | 0.7 cm | 0.4 cm |
| Stipule shape | Acute-bulbous | Elliptical | Scale-like-linear |
| Stipule color (RHS No.) | 149C | 149B | 149A |
| No. of leaflets | 3-9 | 5-7 | 3-5 |
| Middle largest (longest) leaflet length | 13.4 cm | 9.8 cm | 7.6 cm |
| Middle largest (longest) leaflet width | 2.6-7.4 cm | 2.3 cm | 1.8 cm |
| Middle largest (longest) leaflet length/width ratio | 13.4:2.6-13.4:7.4 | 9.8:2.3 | 7.6:1.8 |
| No. teeth of middle leaflet (average) | 29 | 25 | 23 |
| Leaf (upper side) color (RHS No.) | 139A | 132A | 135B |
| Leaf (lower side) color (RHS No.) | 139C | 134D | 135B |
| Leaf glossiness | Weak | Strong | Weak |
| Vein/midrib shape | Obliquely continuous throughout leaflet | Obliquely continuous throughout leaflet | Obliquely continuous throughout leaflet |
| Vein/midrib color | 150D | 144C | 154D |
| Aroma | Citrus zest with chocolate and ginger undertones | Spicy | Earthy, but bitter |

n/a: not available

TABLE 4

| Stem | | | |
|---|---|---|---|
| Characteristics | New Variety | Parental variety (B3) (Female plant) | Parental variety (S9) (Male plant) |
| Stem shape | Hollow, ribbed, large | Hollow, ribbed, textured | Hollow, glandular, ribbed |
| Stem diameter at base | 2.5 cm | 2.8 cm | 1.9 cm |
| Stem color (RHS No.) | 139D | N144D | 195C |
| Depth of main stem ribs/grooves | Shallow | Absent | Medium |
| Internode length | 5.5-11.4 cm | 2.4-4.9 cm | 7.2-14.7 cm |

n/a: not available

TABLE 5

| Inflorescence (Female/Pistillate Flowers) | | | |
|---|---|---|---|
| Characteristics | New Variety | Parental variety (B3) (Female plant) | Parental variety (S9) (Male plant) |
| Flowering (blooming) habit | Elongated compound spikes, from 0.5-2.2 m in length | Cymes, from 0.3-1.0 m in length | Cymes, from 0.8-2.8 m in length |
| Proportion of female plants | 100% | 100% | 100% |
| Inflorescence position | Above | Even | Above |
| Flower arrangement | Cymose (terminal bud matures, while lateral flowers mature thereafter) | Cymose (terminal bud matures, while lateral flowers mature thereafter) | Cymose (terminal bud matures, while lateral flowers mature thereafter) |
| Number of flowers per plant | 50-150 per cyme (i.e. female flower) | 80-120 per cyme | 100-200 per cyme |
| Flower shape | More or less sessile and are borne in racemes; calcaratre-urceolate; a small green bract enclosing the ovary with two long, slender stigmas projecting well above the bract | Calaratre-urceolate a small green bract enclosing the ovary with two long, slender stigmas projecting well above the bract | Calaratre-urceolate a small green bract enclosing the ovary with two long, slender stigmas projecting well above the bract |
| Flower (individual pistillate) length | 0.5 cm | 0.7 cm | 1.0 cm |
| Flower (compound cyme) diameter | 4.5 cm | 3.8 cm | 3.2 cm |
| Bract shape | Urceolate | Urceolate | Urceolate |
| Bract size | 0.4-1.0 cm | 0.2-0.8 cm | 0.4-1.3 cm |
| Bract color (RHS No.) | 142C | N134C | 143C |
| Calyx shape | No defined calyx | No defined calyx | No defined calyx |
| Calyx color (RHS No.) | 142A | 135C | 143C |
| Stigma shape | Linear-lanceolate | Acute | Linear |
| Stigma length | 3.1 mm | 2.2 mm | 5.1 mm |

TABLE 5-continued

| Inflorescence (Female/Pistillate Flowers) | | | |
|---|---|---|---|
| Characteristics | New Variety | Parental variety (B3) (Female plant) | Parental variety (S9) (Male plant) |
| Stigma color (RHS No.) | 157C | 159D | 157D |
| Trichome shape | Capitate-stalked glandular | Capitate-stalked glandular | Capitate-stalked glandular |
| Trichome color (RHS No.) | 157A at day 40 in flowering (capitate-stalked glandular trichomes) | 157A at day 40 in flowering | 157A at day 40 in flowering |
| Other types of trichomes | Capitate sessile trichomes are present on the leaves of plants, as well as being noticed in the flowers (color: 157A at day 40 in flowering). During later flowering, i.e. day 55 to day 70 in flowering, capitate stalked trichomes are present (color: N30B). Bulbous and non-glandular trichomes are also present and most noticeable on the petioles, stems, and leaves (color: 157A). | Capitate sessile trichomes are present on the leaves of plants, as well as being noticed in the flowers (color: 157A at day 40 in flowering). During later flowering, i.e. day 48 to day 60 in flowering, capitate stalked trichomes are present (color: N30B). Bulbous and non-glandular trichomes are also present and most noticeable on the petioles, stems, and leaves (color: 157A). | Capitate sessile trichomes are present on the leaves of plants, as well as being noticed in the flowers (color: 157A at day 40 in flowering). During later flowering, i.e. day 55 to day 70 in flowering, capitate stalked trichomes are present (color: N30B). Bulbous and non-glandular trichomes are also present and most noticeable on the petioles, stems, and leaves (color: 157A). |
| Terminal bud shape | Elliptical | Oblong | Elliptical |
| Terminal bud color (RMS No.) | 136B | 203C | 136D |
| Pedicel | Absent | Absent | Absent |
| Staminate shape | n/a | n/a | n/a |
| Pollen description | Absent | Absent | Absent |
| Seed Shape | Textured and globular | Smooth and globular | Globular |
| Seed size/length | 2.1-2.8 mm | 1.8-2.3 mm, | 2.8-3.3 mm |
| Marbling of seed | Absent (non-existent) | Absent (non-existent) | Absent (non-existent) |
| Petal description | Apetalous (This part is fused and appressed to the base of the ovary with the calyx and the perianth in the cannabis flowers) | Apetalous | Apetalous |
| Petal arrangement | Free | n/a | n/a |
| Max THC content | About 18.77-23.19% | About 18.88-19.37% | About 16.11-18.21% |
| Max CBD content | 0.00% | 0.00% | 0.00% |
| Max CBG content | About 0.98-1.78% | About 0.84-0.91% | About 0.67-0.95% |

n/a: not available

TABLE 6

| Other Characteristics | | | |
|---|---|---|---|
| Characteristics | New Variety | Parental variety (B3) (Female plant) | Parental variety (S9) (Male plant) |
| Time period and condition of flowering/blooming | 9-11 weeks | 7-9 weeks | 9-11 weeks |
| Hardiness of plant | Hardy to 25° F.-ambient temperature | Hardy to 25° F.-ambient temperature | Hardy to 25° F.-ambient temperature |
| Breaking action | Flexible, resistant to breakage | Strong, non-flexible | Flexible, resistant to breakage |
| Rooting rate after cutting/cloning | 99%-vigorous | 70%-moderate | 70%-moderate |
| Types of Cutting for Cloning (stem, leaf, root etc.) | Stem | Stem | Stem |
| Shipping quality if available | High | Moderate | Moderate |
| Storage life if available | Long (3-8 months with minor changes in physical appearance and/or smell taste) | Medium (3-6 months with minor changes in physical appearance and/or smell taste) | Short (1-4 months with minor changes in physical appearance and/or smell taste) |
| Productivity of flower if available | Aprroximately 0.23-0.9 kg can be produced per plant, dependent on finished plant size (1.0-4.0 m); Growing conditions/environment will dictate final yield/output | Aprroximately 0.14-0.45 kg can be produced per plant, dependent on finished plant size (0.6-1.2 m); Growing conditions/environment will dictate final yield/output | Aprroximately 0.09-0.59 kg can be produced per plant, dependent on finished plant size (1.2-4.0 m); Growing conditions/environment will dictate final yield/output |

n/a: not available

LEMON CRUSH OG is larger in width and height than both parents (B3 and S9). LEMON CRUSH OG is more robust in terms of growing performance, time to rooted clones, greater resistance to pest and disease, stronger branches, higher yielding, and overall better performing as it clearly demonstrates hybrid vigor, and therefore outperforms both parents (B3 and S9).

Specifically, when 'LEMON CRUSH OG' is compared to the proprietary female parent ('BLK03'), 'LEMON CRUSH OG' is taller in plant height, but narrower in plant width than 'BLK03'. Generally, 'LEMON CRUSH OG' shows higher plant vigor than 'BLK03'. 'LEMON CRUSH OG' has longer and wider leaflets than 'BLK03' when compared their middle largest leaflet length and width as well as whole leaf length and width. Also, 'LEMON CRUSH OG' has more teeth numbers in middle leaflet than 'BLK03'. Regarding petiole and stipule length at maturity, 'LEMON CRUSH OG' is shorter than 'BLK03'. Regarding stem diameter at base, 'LEMON CRUSH OG' is in general shorter than 'BLK03'. When comparing individual flower length and compound cyme diameter, 'LEMON CRUSH OG' is shorter than 'BLK03' in individual pistillate length, but longer in compound cyme diameter. With respect to aroma, 'LEMON CRUSH OG' has a citrus zest smell with chocolate and ginger undertone, while 'BLK03' has a generally spicy smell.

When 'LEMON CRUSH OG' is compared to the proprietary male parent ('SLV09'), 'LEMON CRUSH OG' is wider than 'SLV09' in plant width. 'LEMON CRUSH OG' shows higher plant vigor than 'SLV09' showing a medium vigor like 'BLK03'. 'LEMON CRUSH OG' has longer and wider leaflets than 'SLV09' when compared their middle largest leaflet length and width. Also, 'LEMON CRUSH OG' has more teeth numbers in middle leaflet than 'BLK03'. Regarding petiole and stipule length at maturity, 'LEMON CRUSH OG' is longer than 'SLV09', opposite to those features of 'BLK03'. Regarding stem diameter at base, 'LEMON CRUSH OG' is something either longer than 'SLV09'. When comparing individual flower length and compound cyme diameter, 'LEMON CRUSH OG' is shorter than 'SLV09' in individual pistillate length, but longer in compound cyme diameter. In terms of aroma, 'LEMON CRUSH OG' has a citrus zest smell with chocolate and ginger undertone, while 'SLV09' has an earthy but bitter smell.

When 'LEMON CRUSH OG' is compared to the known *cannabis* plant named 'ECUADORIAN SATIVA' (U.S. Plant Pat. No. 27,475), there are several distinctive characteristics. For example, 'LEMON CRUSH OG' plant is taller and wider than the 'ECUADORIAN SATIVA' plant. 'LEMON CRUSH OG' plant has a shorter petiole at maturity than the 'ECUADORIAN SATIVA' plant. While the aroma of 'ECUADORIAN SATIVA' is strongly mephitic with hints of limonene, 'LEMON CRUSH OG' has a citrus zest smell with chocolate and ginger undertone. Individual pistillate flowers of 'LEMON CRUSH OG' are slightly longer than those of 'ECUADORIAN SATIVA'. When comparing total THC content between 'LEMON CRUSH OG' and 'ECUADORIAN SATIVA', the total THC content of 'LEMON CRUSH OG' is between 18.77-23.19%, while 'ECUADORIAN SATIVA' accumulates 12.45% total THC.

The following is a detailed description of the new cultivar of 'LEMON CRUSH OG'. The following description is for plants that are 93-100 days old as of the time of the measurements.

General description:

*Plant life form and habit.*—An herbaceous, upright, tap-rooted annual plant.

Classification:

*Denomination.*—'LEMON CRUSH OG'.

*Species.*—*Cannabis* hybrid.

Origin, form, and growth characteristics:

*Origin.*—Progeny of the cross between BLK03 (B3) and SLV09 (S9).

*Propagation.*—The strain is asexually propagated by stem cutting and cloning.

*Propagation ease.*—Easy.

Plant:

*Height.*—1.5-4 m.

*Width.*—89 cm.

*Vigor.*—High (very vigorous).

*Pest susceptibility.*—Resistant to pest as follows; (1) Two-spotted spider mite such as *Tetranychus urticae* (Koch); (2) Aphids species such as *Cannabis* Aphid (*Phorodon cannabis*), Green Peach Aphid (*Myzus persicae* (Sulzer)), Foxglove Aphid (*Aulacorthum solani*), Peach Aphid (*Macrosiphum euphorbiae*), and Black Bean Aphid (*Aphis fabae*); (3) Whitefly (*Trialeurodes vaporariorum*); (4) Lepidoptera species such as Armyworm (*Spodoptera frugiperda*); Cabbage Whites (*Pieris rapae*); Painted Lady (*Vanessa cardui*); and *Lepidoptera* sp.

*Disease susceptibility*.—Resistant to diseases such as *Botrytis*/Flower Rot (*Botrytis cinerea*); Powdery Mildew (*Podosphaera xanthii*).

*Time to harvest*.—11 weeks.

*Genetically modified organism*.—No.

Leaf/foliage:

*Structure*.—Linear-lanceolate leaflet blades with glandular hairs.

*Shape*.—Palmately compound.

*Arrangement*.—Alternate.

*Margin*.—Dentate, coarsely serrated, and the teeth point towards the tip.

*Hair*.—Present.

*Leaf* (*with petiole*) *length at maturity*.—19.1 cm.

*Leaf width at maturity*.—13.5 cm.

*Number of leaflets*.—3-9.

*Middle largest leaflet length*.—13.4 cm.

*Middle largest leaflet width*.—2.6-7.4 cm.

*Middle largest leaflet length/width ration*.—13.4:2.6-13.4:7.4.

*Number of teeth of middle leaflet* (*average*).—29.

*Color*.—Upper side — 139A.

*Color*.—Lower side — 139C.

*Leaf glossiness*.—Weak.

*Veins/midrib shape*.—Obliquely continuous throughout leaflet.

*Vein/midrib color*.—150D.

Petiole:

*Petiole length*.—5.5 cm.

*Petiole color*.—149B.

*Intensity of petiole anthocyanin*.—Absent (vegetative stage); very strong (late flowering stage).

*Stipule shape*.—Acute-bulbous.

*Stipule length*.—0.5 cm.

*Stipule color*.—149C.

Stem:

*Shape*.—Hollow, ribbed, and large.

*Diameter*.—2.5 cm at base.

*Color*.—139D.

*Depth of main stem ribs/grooves*.—Shallow.

*Internode length*.—5.5-11.4 cm.

Inflorescence:

*Blooming/flowering habit*.—Cymes from 0.5-2.2 m in length.

*Inflorescence position relative to foliage*.—Above.

*Flower arrangement*.—Cymose.

*Number of flowers per plant*.—50-150 per Cymes.

Flowers:

*Shape*.—Calcaratre-urceolate calcaratre-urceolate; a small green bract enclosing the ovary with two long, slender stigmas projecting well above the bract.

*Flower* (*individual pistillate*) *length*.—0.5 mm.

*Flower* (*compound cyme*) *diameter*.—4.5 cm.

*Corolla shape*.—The inner envelope of floral leaves of a flower, of delicate texture and of some color other than green.

*Corolla size*.—0.1-0.3 cm.

*Corolla color*.—N/A.

*Bract shape*.—Urceolate.

*Bract size*.—0.4-1.0 cm.

*Bract color*.—142C.

*Stigma shape*.—Linear-lanceolate.

*Stigma length*.—3.1 mm.

*Stigma color*.—157C.

*Trichome shape*.—Capitate-stalked glandular.

*Trichome color*.—157A at day 40 in flowering.

*Other types of trichome*.—Capitate sessile trichomes (color: 157A at day 40 in flowering)are present on the leaves of plants, as well as being noticed in the flowers; During later flowering (day 55 to day 70 in flowering), capitate stalked trichomes (color: N30B) are present; Bulbous and non-glandular trichomes (color: 157A) are also present and most noticeable on the petioles, sterns, and leaves.

*Cola* (*terminal bud*).—Elliptical.

*Cola* (*terminal bud*) *color*.—136B.

*Pedicel*.—Absent.

*Pedicel color*.—N/A.

*Staminate flower*.—N/A.

*Pollen*.—Absent.

*Seed shape*.—Textured and globular.

*Seed size/length*.—2.1 to 2.8 mm.

*Marbling of seed*.—Absent (non-existent).

*Petal*.—Apetalous; This part is fused and appressed to the base of the ovary with the calyx and the perianth in the *cannabis* flowers.

*Petal arrangement*.—Free.

Other characteristics:

*Aroma*.—Citrus zest with chocolate and ginger undertones.

*Flowering/blooming period*.—9-11 weeks.

*Hardiness*.—Hardy to 25° F-ambient temperature.

*Breaking action*.—Flexible, resistant to breakage.

*Rooting rate after cutting/cloning*.—99% vigorous.

*Types of cutting for cloning*.—Stem.

*Shipping quality*.—High.

*Storage life*.—Long (3-8 months with minor changes in physical appearance and/or smell/taste).

*Productivity of flower*.—Approximately 0.23-0.9 kg can be produced per plant, dependent on finished plant size (1.0-4.0 m).

*Market use*.—Medicinal.

The invention claimed is:

1. A new and distinct cultivar of *Cannabis* plant named 'LEMON CRUSH OG' substantially as shown and described herein.

* * * * *

LEMON CRUSH OG

BLK03 (B3)

SLV09 (S9)

LEMON CRUSH OG

BLK03 (B3)

SLV09 (S9)

LEMON CRUSH OG

LEMON CRUSH OG

LEMON CRUSH OG

LEMON CRUSH OG

LEMON CRUSH OG

LEMON CRUSH OG

LEMON CRUSH OG

LEMON CRUSH OG